United States Patent [19]

Wang et al.

[11] Patent Number: 4,877,864
[45] Date of Patent: Oct. 31, 1989

[54] OSTEOINDUCTIVE FACTORS

[75] Inventors: Elizabeth A. Wang, Carlisle; John M. Wozney, Hudson; Vicki Rosen, Boston, all of Mass.

[73] Assignee: Genetics Institute, Inc., Cambridge, Mass.

[21] Appl. No.: 31,346

[22] Filed: Mar. 26, 1987

[51] Int. Cl.$^4$ .................. C07K 7/00; A61K 37/00; C12N 15/00
[52] U.S. Cl. ................................ 530/324; 514/12; 435/172.3; 435/70; 435/320; 935/13
[58] Field of Search ................. 530/324; 514/12; 435/172.3, 70

[56] References Cited

U.S. PATENT DOCUMENTS

| | | |
|---|---|---|
| 4,294,753 | 10/1981 | Urist . |
| 4,434,094 | 2/1984 | Seyedin et al. . |
| 4,455,256 | 6/1984 | Urist ................................ 530/417 |
| 4,563,350 | 1/1986 | Nathan et al. ................ 530/417 |
| 4,608,199 | 8/1986 | Caplan et al. . |
| 4,619,989 | 10/1986 | Urist ................................ 530/417 |
| 4,627,982 | 12/1986 | Seyedin et al. . |
| 4,681,863 | 7/1987 | Nathanson . |
| 4,761,471 | 8/1988 | Urist . |
| 4,774,228 | 9/1988 | Seyedin et al. . |
| 4,774,322 | 9/1988 | Seyedin et al. . |
| 4,789,732 | 12/1988 | Urist . |
| 4,804,744 | 2/1989 | Sen . |

FOREIGN PATENT DOCUMENTS

| | | |
|---|---|---|
| 148155 | 7/1985 | European Pat. Off. . |
| 169016 | 1/1986 | European Pat. Off. . |
| 212474 | 3/1987 | European Pat. Off. . |

OTHER PUBLICATIONS

Urist et al, PNAS USA, vol. 81, pp. 371–375, Jan. 1984.
Hunkapiller et al., Methods in Engymology, vol. 91, pp. 399–413.
Undal et al, PNAS USA, vol. 81, pp. 6481–6485, Oct. 1984.
Lathe, J. Mol. Biol., vol. 183, pp. 1–12 1985.
Frischouf et al, J. Mol. Biol., vol. 170, pp. 827–842.
Kaufman et al, Mol. Cell. Biol., vol. 2, pp. 1304–1319.
Urist, et al., Science 220: 680–686 (1983).
Lucas, et al., Differentiation 37: 47–52 (1988).
Sampath, et al., Proc. Natl. Acad Sci 84: 7109–7113 (1987).

Primary Examiner—Alvin E. Tanenholtz
Attorney, Agent, or Firm—Ellen J. Kapinos; Bruce M. Eisen

[57] ABSTRACT

Human and bovine bone inductive factors are provided. Such factors may be produced by recombinant techniques and be useful in the treatment of bone defects.

7 Claims, No Drawings

OSTEOINDUCTIVE FACTORS

This application is a continuation-in-part of Ser. No. 943,332, filed Dec. 17, 1986, now abandoned and a continuation-in-part of Ser. No. 880,776, filed July 1, 1986 now abandoned.

The present invention relates to novel purified bone inductive factors which demonstrate in vivo activity in inducing cartilage and bone formation, and processes for obtaining such factors.

BACKGROUND

Bone is a highly specialized tissue characterized by an extensive matrix structure formed of fibrous bundles of the protein collagen, and proteoglycans, noncollagenous proteins, lipids and acidic proteins. The processes of bone formation and renewal/repair of bone tissue, which occurs continuously throughout life, are performed by specialized cells. Bone growth is presumably mediated by "osteoblasts" (bone-forming cells), while remodeling of bone is apparently accomplished by the joint activities of bone-resorbing cells, called "osteoclasts" and osteoblasts.

A factor which induces bone growth in circumstances where bone is not normally formed has application in the healing of bone fractures. An osteogenic preparation may have prophylactic use in closed as well as open fracture reduction and also in the improved fixation of artificial joints. De novo bone formation induced by an osteogenic agent would contribute to the repair of congenital, trauma induced, or oncologic resection induced craniofacial defects, and also in cosmetic plastic surgery. Osteogenic factors may be also valuable in the treatment of periodontal disease, and in other tooth repair processes.

Repair of fractures, craniofacial defects, and periodontal defects are presently treated with a bone graft or a synthetic implant. An autograft has highest chance for success, but the trauma of surgery and the quantity of bone that can be harvested are major disadvantages. Allogenic bone grafts are also used. The availability of cadaver bone, the quality of the banked bone, and the potential spread of human disease are serious problems associated with this treatment. Ceramics, such as hydroxylapatite, or metals are also used, but these materials are only osteoconductive, i.e. new bone is generally only formed adjacent to the implant and the normal bone.

Physiologically acceptable chemical agents (hormones/pharmaceuticals/growth factors) capable of inducing bone formation at a predetermined site are therefore desirable. Such agents could provide an environment to attract bone-forming cells, stimulate growth of bone-forming cells or induce differentiation of progenitors of bone-forming cells. A variety of osteogenic, cartilage-inducing and bone inducing factors have been described. See, e.g. European patent application Nos. 148,155 and 169,016 for discussions of the work of others in this field. However, the procedures and techniques known in the art for obtaining putative osteogenic activities are prolonged and ill-defined and the factors have been only minimally identified and poorly characterized.

Thus there remains a need in the art for the accurate chemical and physiological characterization of a highly purified osteoinductive factor of a mammalian species for use in diagnosis, research and therapy of bone formation disorders.

BRIEF DESCRIPTION OF THE INVENTION

As one aspect of the present invention, human bone morphogenic protein compositions substantially free from association with other human proteins is provided. Bovine bone inductive factor substantially free from association with other bovine proteins is also provided.

The human bone inductive protein is characterized by a peptide sequence the same or substantially the same as that of amino acid #1 through amino acid #37 of Table III below. This peptide sequence is encoded by the same or substantially the same DNA sequence, as depicted in nucleotide #3440 through nucleotide #3550 of Table III. The human peptide sequence identified in Table III below is 37 amino acids in length. In this Table, this coding sequence is flanked by approximately 28 nucleotides (a presumptive 5' noncoding sequence) as well as approximately 19 nucleotides (a presumptive 3" noncoding sequence).

The bovine factor is characterized by a peptide sequence containing the same or substantially the same sequence as that of amino acid #1 through amino acid #37, of Table II below. This peptide sequence is encoded by the same or substantially the same DNA sequence as depicted in nucleotide #294 through nucleotide #404 of Table II. The bovine peptide sequence identified in Table II below is also 37 amino acids in length. In Table II this coding sequence is flanked by approximately 21 nucleotides (a presumptive 5' noncoding sequence) as well as approximately 19 nucleotides (a presumptive 3' noncoding sequence).

Bone inductive factor is further characterized by biochemical and biological characteristics including an activity at a concentration of 10 to 1000 ng/gram of bone in an in vivo rat bone formation assay described below. The bovine protein also has an apparent molecular weight of 28–30 kd as determined by sodium dodecyl sulfate polyacrylamide gel electrophoresis (SDS-PAGE), and an isoelectric point of 8.8 to 9.2 determined by isoelectric focusing. Under reducing conditions in SDS polyacrylamide gel electrophoresis, the bovine bone inductive protein composition reveals two major bands of approximately 18 and 20 kd and a less abundant protein band at approximately 30 kd.

DNA sequences which hybridize to the coding sequence of Table II or III under relaxed hybridization conditions and which code on expression for osteoinductive factors having at least one of the above-recited biological properties also encode bone inductive factors according to this invention. For example, a DNA sequence which shares regions of significant homology with the coding sequence of Table II and encodes a protein having one or more of the recited biological properties of a bone inductive factor clearly encodes a bone inductive factor of the invention, even if such a DNA sequence would not stringently hybridize to the sequence of Table II. For example, the human protein sequence of Table III is approximately 84% homologous to the bovine protein. The DNA sequence encoding it thereby hybridizes less than strictly thereto, but encodes a bone inductive protein of human origin.

Slight variations in the sequences of Tables II and III which are caused by point mutations, naturally occurring allelic genes and induced modifications should not change the functional proteins for which the sequences code on expression. Such variations may be expected to enhance the activity or production of the osteoinductive factors. Such modifications to the sequences, including those due to the degeneracies of the genetic code, are encompassed in the invention. Nucleotide modifications can be deliberately engineered into the DNA sequences employed in this method, which modifications can be made by one skilled in the art using known techniques. Such modifications can include the deletion, insertion or substitution of amino acids. Mutagenic techniques for such replacement or deletion are well known to one skilled in the art. [See, U.S. Pat. No. 4,518,584].

Similarly, synthetic factors which wholly or partially duplicate continuous sequences of the amino acid residues identified in Table II or III are also part of this invention. These sequences, by virtue of sharing primary, secondary or tertiary structural and conformational characteristics with naturally-occurring bovine or human osteoinductive factor may possess biological activity and/or biochemical properties in common with the naturally-occurring product. Thus, they may be employed as biologically active substitutes for naturally-occurring osteoinductive factors in therapeutic processes.

As another aspect of the present invention, there is provided a novel method for producing the novel osteoinductive factors. The method of the present invention involves culturing a suitable cell or cell line, which has been transformed with a DNA sequence coding on expression for a novel osteoinductive factor of the present invention under appropriate expression control sequences. The selection of suitable host cells and methods for transformation, culture, amplification, screening and product production and purification are known in the art. See, e.g. Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446. Suitable cells or cell lines may be mammalian cells, such as Chinese hamster ovary cells (CHO). Another suitable mammalian cell line, which is described in the accompanying examples, is the monkey COS-1 cell line. A similarly useful mammalian cell line is the CV-1 cell line.

Also suitable for use in the present invention are bacterial cells. For example, the various strains of *E. coli* are well-known as host cells in the field of biotechnology. Various strains of *B. subtilis* may also be employed in this method. Many strains of yeast cells known to those skilled in the art are also available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

Another aspect of the present invention provides vectors for use in the method of expression of these novel osteoinductive factors. These vectors contain the same, or substantially the same, nucleotide sequence as the sequence of nucleotide #3440 through #3550 as depicted in Table III or nucleotide #294 through #404 as depicted in Table II. Preferably the vectors contain the full novel DNA sequences described above which code for the novel factors of the invention. Additionally the vectors also contain appropriate expression control sequences permitting expression of the bone inductive factor sequences. Alternatively, vectors incorporating modified sequences as described above are also embodiments of the present invention and useful in the production of the bone inductive factors. The vectors may be employed in the method of transforming cell lines and contain selected regulatory sequences in operative association with the DNA coding sequences of the invention which are capable of directing the replication and expression thereof in selected host cells. Useful regulatory sequences for such vectors are known to one of skill in the art and may be selected depending upon the selected host cells. Such selection is routine and does not form part of the present invention.

As still a further aspect of the invention is a therapeutic method and composition for repairing fractures and other conditions related to bone defects or periodontal diseases. Such a composition comprises a therapeutically effective amount of a bone inductive factor protein composition of the invention. The bone inductive factor according to the present invention may be present in a therapeutic composition in admixture with a pharmaceutically acceptable carrier or matrix. Additionally, a factor according to the present invention may be co-administered with one or more different osteoinductive factors, with which it may interact. Further, the therapeutic composition may be combined with other agents beneficial to the treatment of the bone defect in question.

The therapeutic method includes locally administering the composition as an implant or device. When administered, the therapeutic composition for use in this invention is, of course, in a pyrogen-free, physiologically acceptable form. Preferably, the bone growth inductive factor composition would include a matrix capable of delivering the bone inductive factor to the site of bone damage, providing a structure for the developing bone and cartilage and optimally capable of being resorbed into the body. Such matrices may be formed of other materials presently in use for other implanted medical applications.

The bone inductive factor composition can also alternatively include other osteoconductive materials, such as hydroxylapatite, ceramics and the like. Further, the composition may desirably be encapsulated or injected in a viscous form for delivery to the site of bone damage. The preparation of such physiologically acceptable protein compositions, having due regard to pH, isotonicity, stability and the like, is within the skill of the art.

The dosage regimen will be determined by the attending physician considering various factors which modify the action of such a growth factor, e.g. amount of bone weight desired to be formed, the site of bone damage, the condition of the damaged bone, the patient's age, sex, and diet, the severity of any infection, time of administration and other clinical factors. Generally, the dosage regimen should be in the range of approximately 10 to $10^6$ nanograms of protein per gram of bone weight desired. Progress can be monitored by periodic assessment of bone growth and/or repair, e.g. x-rays. Such therapeutic compositions are also presently valuable for veterinary applications due to the lack of species specificity in bone inductive factors. Particularly domestic animals and thoroughbred horses are desired patients for such treatment with the bone inductive factor of the present invention.

DETAILED DESCRIPTION OF THE INVENTION

The following examples illustrate practice of the present invention in recovering and characterizing the bovine bone inductive factor, employing the bovine bone inductive factor to recover human bone inductive factor, obtaining the human factor and in expressing the bone inductive factors via recombinant techniques.

EXAMPLE I

Isolation of Bovine Bone Inductive Factor

Ground bovine bone powder (20-120 mesh, Helitrex) is prepared according to the procedures of M. R. Urist et al., *Proc Natl Acad. Sci USA*, 70:3511 (1973) with elimination of some extraction steps as identified below. Ten kgs of the ground powder is demineralized in successive changes of 0.6N HCl at 4° C. over a 48 hour period with vigorous stirring. The resulting suspension is extracted for 16 hours at 4° C. with 50 liters of 2M $CaCl_2$ and 10 mM ethylenediaminetetraacetic acid [EDTA], and followed by extraction for 4 hours in 50 liters of 0.5M EDTA. The residue is washed three times with distilled water before its resuspension in 20 liters of 4M guanidine hydrochloride [GuCl], 20 mM Tris (pH 7.4), 1 mM N-ethylmaleimide, 1 mM iodoacetamide, 1 mM phenylmethylsulfonyl fluorine as described in *Clin. Orthop. Rel. Res.*, 171: 213 (1982). After 16 to 20 hours the supernatant is removed and replaced with another 10 liters of GuCl buffer. The residue is extracted for another 24 hours.

The crude GuCl extracts are combined, concentrated approximately 20 times on a Pellicon apparatus with a 10,000 molecular weight cut-off membrane, and then dialyzed in 50 mM Tris, 0.1 M NaCl, 6 M urea (pH7.2), the starting buffer for the first column. After extensive dialysis the protein is loaded on a 4 liter DEAE cellulose column and the unbound fractions are collected.

The unbound fractions are concentrated and dialyzed against 50 mM NaAc, 50 mM NaCl (pH 4.6) in 6M urea. The unbound fractions are applied to a carboxymethyl cellulose column. Protein not bound to the column is removed by extensive washing with starting buffer, and the bone inductive factor containing material desorbed from the column by 50 mM NaAc, 0.25 mM NaCl, 6M urea (pH 4.6). The protein from this step elution is concentrated 20- to 40- fold, then diluted 5 times with 80 mM $KPO_4$, 6M urea (pH6.0). The pH of the solution is adjusted to 6.0 with 500 mM $K_2HPO_4$. The sample is applied to an hydroxylapatite column (LKB) equilibrated in 80 mM $KPO_4$, 6M urea (pH6.0) and all unbound protein is removed by washing the column with the same buffer. Bone inductive factor activity is eluted with 100 mM $KPO_4$ (pH7.4) and 6M urea.

The protein is concentrated approximately 10 times, and solid NaCl added to a final concentration of 0.15M. This material is applied to a heparin—Sepharose column in equilibrated 50 mM $KPO_4$, 150 mM NaCl, 6M urea (pH7.4). After extensive washing of the column with starting buffer, a protein with bone inductive factor activity is eluted by 50 mM $KPO_4$, 700 mM NaCl, 6M urea (pH7.4). This fraction is concentrated to a minimum volume, and 0.4 ml aliquots are applied to Superose 6 and Superose 12 columns connected in series, equilibrated with 4 M GuCl, 20 mM Tris (pH7.2) and the columns developed at a flow rate of 0.25 ml/min. The protein demonstrating bone inductive factor activity has a relative migration corresponding to approximately 30,000 dalton protein.

The above fractions are pooled, dialyzed against 50 mM NaAc, 6M urea (pH4.6), and applied to a Pharmacia MonoS HR column. The column is developed with a gradient to 1.0M NaCl, 50 mM NaAc, 6M urea (pH4.6). Active fractions are pooled and brought to pH3.0 with 10% trifluoroacetic acid (TFA). The material is applied to a 0.46×25 cm Vydac C4 column in 0.1% TFA and the column developed with a gradient to 90% acetonitrile, 0.1% TFA (31.5% acetonitrile, 0.1% TFA to 49.5% acetonitrile, 0.1% TFA in 60 minutes at 1 ml per minute). Active material is eluted at approximately 40-44% acetonitrile. Aliquots of the appropriate fractions are iodinated by one of the following methods: P. J. McConahey et al, *Int. Arch. Allergy*, 29:185-189 (1966); A. E. Bolton et al, *Biochem J.*, 133:529 (1973); and D. F. Bowen-Pope, *J. Biol. Chem.*, 237:5161 (1982). The iodinated proteins present in these fractions are analyzed by SDS gel electrophoresis and urea Triton X 100 isoelectric focusing. At this stage, the bone inductive factor is estimated to be approximately 10-50% pure.

EXAMPLE II

Characterization of Bovine Bone Inductive Factor

A. Molecular Weight

Approximately 20 μg protein from Example I is lyophilized and redissolved in 1X SDS sample buffer. After 15 minutes of heating at 37° C., the sample is applied to a 15% SDS polyacrylamide gel and then electrophoresed with cooling. The molecular weight is determined relative to prestained molecular weight standards (Bethesda Research Labs). Immediately after completion, the gel lane containing bone inductive factor is sliced into 0.3 cm pieces. Each piece is mashed and 1.4 ml of 0.1% SDS is added. The samples are shaken gently overnight at room temperature to elute the protein. Each gel slice is desalted to prevent interference in the biological assay. The supernatant from each sample is acidified to pH 3.0 with 10% TFA, filtered through a 0.45 micron membrane and loaded on a 0.46 cm×5 cm C4 Vydac column developed with a gradient of 0.1% TFA to 0.1% TFA, 90% $CH_3CN$. The appropriate bone inductive factor - containing fractions are pooled and reconstituted with 20 mg rat matrix as previously described. In this gel system, the majority of bone inductive factor fractions have the mobility of a protein having a molecular weight of approximately 28,000-30,000 daltons.

B. Isoelectric Focusing

The isoelectric point of bone inductive factor activity is determined in a denaturing isoelectric focusing system. The Triton X100 urea gel system (Hoeffer Scientific) is modified as follows: (1) 40% of the ampholytes used are Servalyte 3/10; 60% are Servalyte 7-9. (2) The catholyte used is 40 mM NaOH. Approximately 20 μg of protein from Example I is lyophilized, dissolved in sample buffer and applied to the isoelectrofocusing gel. The gel is run at 20 watts, 10° C. for approximately 3 hours. At completion the lane containing bone inductive factor is sliced into 0.5 cm slices. Each piece is mashed in 1.0 ml 6M urea, 5 mM Tris (pH 7.8) and the samples agitated at room temperature. The pH gradient of the gel is determined by soaking 5 mm slices in 1.0 ml water for over 2 hours. The samples are acidified, filtered, desalted and assayed as described above. The major portion of activity as determined in the assay described in Example III migrates in a manner consistent with a pI of 8.8-9.2.

C. Subunit Characterization

The subunit composition of bone inductive factor is also determined. Pure bone inductive factor is isolated from a preparative 15% SDS gel as described above. A portion of the sample is then reduced with 5 mM DTT in sample buffer and re-electrophoresed on a 15% SDS gel. The approximately 30 kd protein yields two major bands at approximately 20 kd and 18 kd, as well as a minor band at 30 kd. The broadness of the two bands indicates heterogeneity caused most probably by glycosylation, other post translational modification, proteolytic degradation or carbamylation.

EXAMPLE III

Biological Activity of Bone Inductive Factor

A rat bone formation assay according to the general procedure of Sampath and Reddi, *Proc. Natl. Acad. Sci. U.S.A.*, 80:6591-6595 (1983) is used to evaluate the osteogenic activity of the bovine bone inductive factor of the present invention. The ethanol precipitation step is replaced by dialyzing the fraction to be assayed against water. The solution or suspension is then redissolved in a volatile solvent, e.g. 0.1-0.2 % TFA, and the resulting solution added to 20 mg of rat matrix. This material is frozen and lyophilized and the resulting powder enclosed in #5 gelatin capsules. The capsules are implanted subcutaneously in the abdominal thoracic area of 21-49 day old male long Evans rats. The implants are removed after 7-14 days. Half of each implant is used for alkaline phosphatase analysis [See, A. H. Reddi et al., *Proc. Natl Acad Sci.*, 69:1601 (1972)] and half is fixed and processed for histological analysis. Routinely, lum glycolmethacrylate sections are stained with Von Kossa (specific for mineralization) and acid fuschin and visually scored on a relative scale of 0 to 5 for new bone and cartilage formation and mineralization. Alkaline phosphatase is an enzyme formed as cartilage calcifies and bone starts to form and its measurement enables the tracking of new bone and cartilage formation. The alkaline phosphatase levels in the assay reveal that the bone inductive factor stimulates new bone and cartilage growth in the implants. Table I below illustrates the dose response of the rat matrix samples including a control not treated with bone inductive factor.

TABLE I

| Protein* Implanted ug | Cartilage | Alk. Phos.u/l |
| --- | --- | --- |
| 7.5 | 2 | Not done |
| 2.5 | 3 | 445.7 |
| 0.83 | 3 | 77.4 |
| 0.28 | 0 | 32.5 |
| 0.00 | 0 | 31.0 |

*At this stage the bone inductive factor is approximately 10-15% pure.

Samples are also analyzed by SDS gel electrophoresis and isoelectric focusing as described above, followed by autoradiography. Analysis reveals a correlation of activity with protein bands at 28-30 kd and a pI 9.0. An extinction coefficient of 1 OD/mg-cm is used as an estimate for protein and approximating the purity of bone inductive factor in a particular fraction. In the in vivo rat bone formation assays on dilutions as described above, the protein is active in vivo at 100 to 200 ng protein/gram bone to probably greater than 1ug protein/gram bone.

EXAMPLE IV

Bovine Bone Inductive Factor Protein Composition

The protein composition of Example IIA is reduced as described in Example IIB and digested with trypsin. Eight tryptic fragments are isolated having the following amino acid sequences:

| | |
| --- | --- |
| Fragment 1 | A A F L G D I A L D E E D L G |
| Fragment 2 | A F Q V Q Q A A D L |
| Fragment 3 | N Y Q D M V V E G |
| Fragment 4 | S T P A Q D V S R |
| Fragment 5 | N Q E A L R |
| Fragment 6 | L S E P D P S H T L E E |
| Fragment 7 | F D A Y Y |
| Fragment 8 | L K P S N ? A T I Q S I V E |

Probes consisting of pools of oligonucleotides (or unique oligonucleotides) are designed according to the method of R. Lathe, *J. Mol. Biol.*, 183 (1):1-12 (1985) and synthesized on an automated DNA synthesizer. One probe consists of a relatively long (32 nucleotides) "guessmer" [See J. J. Toole et al, *Nature*, 312:342-347 (1984)] of the following nuleotide sequence:

TCCTCATCCAGGGCAATGTCGCCCAG-GAAGGC

Because the genetic code is degenerate (more than one codon can code for the same amino acid), the number of oligonucleotides in a probe pool is reduced based on the frequency of codon usage in eukaryotes, the relative stability of G:T base pairs, and the relative infrequency of the dinucleotide CpG in eukaryotic coding sequences [see Toole et al., supra.]. The second set of probes consists of shorter oligonucleotides (17 nucleotides in length) which contain all possible sequences that could encode the amino acids. The second set of probes has the following sequences:

(a) A [A/G] [A/G] TC [T/C] TC [T/C] TC [A/G] TC [T/C] AA (b) A [A/G] [A/G] TC [T/C] TC [T/C] TC [A/G] TCNAG

Bracketed nucleotides are alternatives. "N" means either A, T, C or G.

In both cases the regions of the amino acid sequence used for probe design are chosen by avoiding highly degenerate codons where possible The oligonucleotides are synthesized on an automated DNA synthesizer; the probes are then radioactively labeled with polynucleotide kinase and $^{32}$P-ATP.

These two sets of probes are used to screen a bovine genomic recombinant library. The library is constructed as follows: Bovine liver DNA is partially digested with the restriction endonuclease enzyme Sau 3A and sedimented through a sucrose gradient. Size fractionated DNA in the range of 15-30 kb is then ligated to the bacteriophage Bam HI vector EMBL3 [Frischauf et al, *J. Mol. Biol.*, 170:827-842 (1983)]. The library is plated at 8000 recombinants per plate. Duplicate nitrocellulose replicas of the plaques are made and amplified according to the procedure of Woo et al, *Proc. Natl. Acad. Sci. USA*, 75:3688-91 (1978).

The 32 mer probe is kinased with 32P-gamma-ATP and hybridized to one set of filters in 5X SSC, 0.1% SDS, 5X Denhardts, 100 µg/ml salmon sperm DNA at 45 degrees C. and washed with 5X SSC, 0.1% SDS at 45 degrees C. The 17 mer probes are kinased and hybridized to the other set of filters in 3M tetramethylammonium chloride (TMAC), 0.1M sodium phosphate pH6.5, 1 mM EDTA, 5X Denhardts, 0.6% SDS, 100 µg/ml salmon sperm DNA at 48 degrees C., and washed in 3M TMAC, 50 mM Tris pH8.0 at 50 degrees C. These conditions minimize the detection of mismatches to the 17 mer probe pool [see, Wood et al, *Proc.*

*Natl. Acad. Sci, U.S.A.*, 82:1585–1588 (1985)]. 400,000 recombinants are screened by this procedure and one duplicate positive is plaque purified. DNA is isolated from a plate lysate of this recombinant bacteriophage designated lambda bP-50. bP-50 is on deposit with the American Type Culture Collection, 12301 Parklawn Drive, Rockville, Md. under accession number 40295.

The oligonucleotide hybridizing region of this clone is localized to an approximately 800 bp Eco RI fragment which is subcloned into M13 and sequenced by standard techniques. The partial DNA sequence and derived amino acid sequence of lambda bP-50 are shown below in Table II. The amino acid sequences corresponding to the tryptic fragments isolated from the bovine bone 28 to 30 kd material are underlined in Table II. The first underlined portion of the sequence corresponds to tryptic fragment 1 above from which the oligonucleotide probes are designed. The second underlined portion corresponds to tryptic fragment 2 above. The predicted amino acid sequence indicates that tryptic fragment 2 is preceded by a basic residue (R) as expected considering the specificity of trypsin. The nucleic acid sequence preceding the couplet CT at nucleotide positions #292–293 in Table II is presumed to be an intron (noncoding sequence) based on the presence of a consensus acceptor sequence (i.e., an oligopyrimidine tract, TCTCTCTCC, followed by AG) and the lack of a basic residue in the appropriate position of the derived amino acid sequence. The peptide sequence from this clone is 37 amino acids in length and is encoded by the DNA sequence from nucleotide #294 through #404.

bovine DNA sequence of Table II (or portions thereof) was used as a probe to screen a human genomic library. The 800 bp EcoRI fragment of the bovine genomic clone is labeled with $^{32}P$ by nick-translation. A human genomic library (Toole et al., supra) is plated on 20 plates at 40,000 recombinants per plate. Duplicate nitrocellulose filter replicas are made of each plate and hybridized to the nick-translated probe in 5 X SSC, 5 X Denhardt's, 100 µg/ml denatured salmon sperm DNA, 0.1% SDS at 50 degrees centigrade for approximately 14 hours. The filters are then washed in 1 X SSC, 0.1% SDS at 50 degrees centigrade and subjected to autoradiography. Five duplicate positives are isolated and plaque purified. DNA is obtained from a plate lysate of one of these recombinant bacteriophage, designated LP-Hl. The hybridizing region of LP-HI is localized to a 2.5 kb XbaI/HindIII restriction fragment. The partial DNA sequence and derived amino acid sequence of lambda LP-Hl are shown below in Table III. LP-Hl has been deposited with the American Type Culture Collection under accession number 40311.

Because the size of coding regions and the positions of noncoding regions is generally conserved in homologous genes of different species, the locations of the coding and noncoding regions of the bone inductive factor genes may be identified. Regions of homology between the two species' genes, flanked by RNA processing signals at homologous sites, indicate a coding region.

TABLE III

```
                                                           3419           3429
                                                      CAGCCCTGGC TTCTTCTTTT 3439  (1)              3454                3469                3484
     CTCTTTAGCT GCC TTT CTT GGG GAC ATT GCC CTG GAC GAA GAG GAC CTG AGG GCC
                Ala Phe Leu Gly Asp Ile Ala Leu Asp Glu Glu Asp Leu Arg Ala 3499                3514                3529
     TTC CAG GTA CAG CAG GCT GTG GAT CTC AGA CGG CAC ACA GCT CGT AAG TCC TCC
     Phe Gln Val Gln Gln Ala Val Asp Leu Arg Arg His Thr Ala Arg Lys Ser Ser 3544    (37)      3560           3570
     ATC AAA GCT GCA GGTAAGCCGG GTGCCAATGG
     Ile Lys Ala Ala
```

The human coding sequence of LP-Hl is used as a probe to identify a human cell line or tissue which synthesizes bone inductive factor. Briefly described, RNA

TABLE II

```
                                         280
                                    CCTTGCCTCT 290  (1)           308                 323
     TCTCTCTCCA GCT GCC TTC CTT GGG GAC ATC GCC CTG GAC GAG GAG GAC TTG AGG
                Ala Phe Leu Gly Asp Ile Ala Leu Asp Glu Glu Asp Leu Arg 338              353                 368                 383
     GCC TTC CAA GTG CAG CAG GCT GCG GAC CTC AGA CAG CGT GCA ACC CGC AGG TCT
     Ala Phe Gln Val Gln Gln Ala Ala Asp Leu Arg Gln Arg Ala Thr Arg Arg Ser 398    (37)    414       424
     TCC ATC AAA GCT GCA GGTACACTGG GTACAGGCCA
     Ser Ile Lys Ala Ala
```

EXAMPLE V

Human Bone Inductive Factor

Because the bovine and human bone growth factor genes are presumed to be significantly homologous, the is extracted from a selected cell or tissue source and either electrophoresed on a formaldehyde agarose gel and transferred to nitrocellulose, or reacted with formaldehyde and spotted on nitrocellulose directly. The nitrocellulose is then hybridized to a probe derived from a coding sequence in the human bone inductive factor gene. mRNA is selected by oligo (dT) cellulose chromatography and cDNA is synthesized and cloned in lambda gt10 by established techniques (Toole et al., supra).

Alternatively, the entire gene encoding human bone inductive factor can be identified and obtained in additional recombinant clones if necessary. Additional recombinants containing further 3' or 5' regions of the human bone inductive factor gene can be obtained by identifying unique DNA sequences at the end(s) of the original clone and using these as probes to rescreen the human genomic library. The gene can then be reassembled in a single plasmid by standard molecular biology techniques and amplified in bacteria. The entire human bone inductive factor gene can then be transferred to an appropriate expression vector. The expression vector containing the gene is then transfected into a mammalian cell, e.g. monkey COS cells, where the human gene is transcribed and the RNA correctly spliced. Media from the transfected cells are assayed for bone inductive factor activity as described above for the bovine bone inductive factor as an indication that the gene is complete. mRNA is obtained from these cells and cDNA synthesized from this mRNA source and cloned. This procedure has been described for the cloning and expression of erythropoietin by Lin et al., supra.

EXAMPLE VI

Expression of Bone Inductive Factors.

In order to produce bovine, human or other mammalian bone inductive factor, the DNA encoding it is transferred into an appropriate expression vector and introduced into mammalian cells by conventional genetic engineering techniques.

One skilled in the art can construct mammalian expression vectors by employing the sequence of Table II or Table III or other modified sequences and known vectors, such as pCD [Okayama et al., *Mol. Cell Biol.*, 2:161-170 (1982)] and pJL3, pJL4 [Gough et al., *EMBO J.*, 4:645-653 (1985)]. The transformation of these vectors into appropriate host cells can result in expression of osteoinductive factors. One skilled in the art could manipulate the sequence of Table II or III by eliminating or replacing the mammalian regulatory sequences flanking the coding sequence with bacterial sequences to create bacterial vectors for intracellular or extracellular expression by bacterial cells. For example, the coding sequence of Table II or III could be further manipulated (e.g. ligated to other known linkers or modified by deleting non-coding sequences therefrom or altering nucleotides therein by other known techniques). The modified bone inductive factor coding sequence could then be inserted into a known bacterial vector using procedures such as described in T. Taniguchi et al., *Proc. Natl Acad. Sci. USA*, 77:5230-5233 (1980). This exemplary bacterial vector could then be transformed into bacterial host cells and bone inductive factor expressed thereby. For a strategy for producing extracellular expression of bone inductive factor in bacterial cells., see, e.g. European patent application EPA No. 177,343.

Similar manipulations can be performed for the construction of an insect vector [See, e.g. procedures described in published European patent application No. 155,476] for expression in insect cells. A yeast vector could also be constructed employing yeast regulatory sequences for intracellular or extracellular expression of the factors of the present invention by yeast cells. [See, e.g., procedures described in published PCT application No. WO86/00639 and European patent application EPA No. 123,289].

A method for producing high levels of an osteoinductive factor of the invention from mammalian cells involves the construction of cells containing multiple copies of the heterologous bone inductive factor gene. The heterologous gene can be linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159:601-629 (1982). This approach can be employed with a number of different cell types.

For example, a plasmid containing the bovine bone inductive factor gene of Table II in operative association with other plasmid sequences enabling expression thereof and the DHFR expression plasmid pAdA26SV-(A)3 [Kaufman and Sharp, *Mol. Cell. Biol.*, 2:1304 (1982)] can be co-introduced into DHFR-deficient CHO cells, DUKX-BII, by calcium phosphate coprecipitation and transfection. DHFR expressing transformants are selected for growth in alpha media with dialyzed fetal calf serum, and subsequently selected for amplification by growth in increasing concentrations of MTX (sequential steps in 0.02, 0.2, 1.0 and 5 μM MTX) as described in Kaufman et al., *Mol Cell Biol.*, 5:1750 (1983). Transformants are cloned, and biologically active bone inductive factor expression is monitored by rat bone formation assay. Bone inductive factor expression should increase with increasing levels of MTX resistance. Similar procedures can be followed to produce other bone inductive factors.

Alternatively, the human gene is expressed directly, as described above. Active bone inductive factor may be produced in bacteria or yeast cells. However the presently preferred expression system for biologically active recombinant human bone inductive factor is stably transformed CHO cells.

Similarly the procedures described above may be employed to isolate other species' bone inductive factor of interest by utilizing the bovine bone inductive factor and/or human bone inductive factor as a probe source. Such other species' bone inductive factor may find similar utility in, inter alia, fracture repair.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. A purified cartilage and bone inductive protein produced by the steps comprising:
    (a) culturing a cell transformed with a DNA sequence comprising the sequences as follows; GCC TTT CTT GGG GAC ATT GCC CTG GAC GAA GAG GAC CTG AGG GCC TTC CAG GTA CAG CAG GCT GTG TAT CTC AGA CGG CAC ACA GCT CGT AAG TCC TCC ATC AAA GCT GCA, naturally occuring allelic sequences thereof, equivalent degenerative codon sequences thereof or sequences which (1) hybridize thereto under stringent hybridization condition; and
(2) upon expression encode a protein characterized by the ability to induce bone and/or cartilage formation in the in vivo rat bone formation assay at a concentration of between about 10–1000 nanograms per gram bone; and (b) recovering and purifying from said culture medium said protein so as to be substantially free from association with other proteinaceous materials and characterized by a peptide sequence comprising the following sequence; Ala Phe Leu Gly Asp Ile Ala Leu Asp Glu Glu Asp Leu Arg Ala Phe Gln Val Gln Gln Ala Val Asp Leu Arg Arg His Thr Ala Arg Lys Ser Ser Ile Lys Ala Ala, and naturally occuring allelic sequences thereof.

2. A protein according to claim 1, further characterized by cartilage and/or bone growth stimulating activity in the in vivo rat bone formation assay at a concentration of between about 10 to about 1000 nanograms per gram of bone.

3. A protein according to claim 1, further characterized by
(a) an apparent molecular weight of 28 to 30 kd as determined by SDS-polyacrylamide gel electrophoresis; and
(b) an isoelectric point of between about pH 8.8–9.2 as determined by isoelectric focusing.

4. A therapeutic composition for treating cartilage and/or bone defects comprising an effective amount of a protein of claim 1 in a pharmaceutically acceptable vehicle.

5. A composition according to claim 4 further comprising a matrix for delivering the protein to the site of the cartilage and/or bone defect.

6. A method for treating cartilage and/or bone defects comprising administering an effective amount of a composition of claim 4.

7. A method for treating cartilege and/or bone defects comprising administering an effective amount of a composition of claim 5.

* * * * *